United States Patent [19]

Piso et al.

[11] 4,300,094
[45] Nov. 10, 1981

[54] FINISH MEASURING METHOD AND APPARATUS

[75] Inventors: John S. Piso, Framingham; James K. Roberge, Lexington, both of Mass.

[73] Assignee: Micro Sensors, Inc., Holliston, Mass.

[21] Appl. No.: 900,611

[22] Filed: Apr. 27, 1978

[51] Int. Cl.³ .................. G01R 27/02; G01L 5/04
[52] U.S. Cl. ............................... 324/65 R; 73/160; 324/65 P; 427/10
[58] Field of Search .............. 324/65 R, 65 P, 64, 324/57 R, 62; 73/160; 57/264, 265; 427/8, 9, 10

[56] References Cited

U.S. PATENT DOCUMENTS

| | | | |
|---|---|---|---|
| 2,008,046 | 7/1935 | Snelling | 324/65 R |
| 2,476,943 | 7/1949 | Brady | 324/64 |
| 2,586,868 | 2/1952 | Scott | 324/64 |
| 2,854,626 | 9/1958 | Davidson et al. | 324/64 |
| 3,535,631 | 10/1970 | DeGeest et al. | 324/65 R |
| 3,602,190 | 8/1971 | Kral, Jr. | 324/65 R X |
| 3,859,594 | 1/1975 | Gridheim | 324/65 R X |
| 3,890,567 | 6/1975 | Knufflmann et al. | 324/64 |
| 3,927,842 | 12/1975 | Droll | 324/65 R X |

FOREIGN PATENT DOCUMENTS

371998 3/1923 Fed. Rep. of Germany ........ 324/64

*Primary Examiner*—Ernest F. Karlsen
*Attorney, Agent, or Firm*—Parmelee, Johnson, Bollinger & Bramblett

[57] ABSTRACT

The amount of electrically conductive finish that has been applied to a filament is determined by measuring the conductance of a length of the filament. The measurements are made independently of any differences in conductivity of finish mediums by means of a reference cell containing a sample of the particular finish medium used. An electric measurement circuit provides an indication of the amount of finish medium on the filament by determining the ratio of the conductance of the length of filament to the conductance of the reference cell. In one circuit embodiment, two operational amplifiers are placed in series. The reference cell takes the place of the feedback resistor of one operational amplifier and the length of filament takes the place of the input resistance of the other amplifier. The resulting output of the series circuit is a scaled ratio of the conductances of the finish along the length of filament and in the cell. In another circuit embodiment, voltages applied through the length of filament and reference cell are selectively switched into a dual slope integrating circuit. In its preferred form, the finish measuring apparatus is a hand-held device having contacts which may be connected to a filament using a trigger mechanism.

32 Claims, 11 Drawing Figures

FINISH MEASURING METHOD AND APPARATUS

BACKGROUND OF THE INVENTION

This invention relates to a method and apparatus for measuring the quantity of a finish medium coated on or dispersed through a fiber and more particularly to measuring electrically conductive finishes applied to the filament.

It is common quality control practice to periodically measure the amount of finish on a filament after the filament has passed through a finish applicator. Often, a sample of the filament is cut from the system and chemically tested in a laboratory. Such methods not only cause a delay in the overall operation when a sample filament is extracted from the system, they also result in a long delay before the results are received. Further, past methods do not permit continuous monitoring of the finish or selective trouble shooting throughout a system.

An object of this invention is to provide a finish measuring apparatus for continuously or selectively monitoring the amount of finish on a moving filament within a system without the need for interfering with the continued system operation.

Another object of the invention is to provide such a finish measuring apparatus the calibration of which requires no preliminary laboratory analysis of the particular finishing medium used.

SUMMARY

In accordance with the invention in one of its aspects, the moving filament is slidingly contacted by first and second spaced electrical contact elements. The amount of electrically conductive medium applied to the filament is determined as a function of the conductance of the filament between the contact elements.

In accordance with a further aspect of the invention, the measuring apparatus includes a reference cell containing a sample of the electrically conductive medium used as a filament finish. The amount of finish on the filament is determined in an electrical circuit as a function of the ratio of the conductance of the length of filament between the electrical contact elements and the conductance of the sample cell.

In accordance with another aspect of the invention, the measuring apparatus is a hand-held device which includes means for grasping the filament and holding the filament in sliding contact with each of the filament contact elements.

In a preferred circuit, the length of the filament is connected as the input resistance to an operational amplifier and the reference cell is connected as the feedback resistance of another operational amplifier in series with the first. The output of the circuit is a signal proportional to the ratio of the conductances of the length of filament and of the reference cell.

In accordance with another circuit, voltages are alternately applied through the length of filament and the sample cell to a dual slope integrating circuit arrangement for determining the ratio of the conductances.

DESCRIPTION OF PREFERRED EMBODIMENTS OF THE INVENTION

Two instruments are described herein. Both instruments are used in an on-line mode; that is, each monitors the moving filament without interfering with operation of the system. In the first instrument a low cost transducer arrangement is permanently positioned at each threadline. The second instrument is a hand-held, battery-powered apparatus having more sophisticated circuitry which can be used to measure any threadline within the system. This latter instrument is particularly suitable for trouble shooting, whereas the first is most suitable for continuous quality control monitoring.

Both instruments make use of the linear relationship between the conductance of a length of fiber coated with, or otherwise containing, a conducting medium and the quantity of conducting medium present on a per unit length basis.

It is assumed that the conductivity of the fiber itself is insignificant compared with the conductivity of the conducting medium. The conducting medium may be an external coating on the fiber, or it may be dispersed throughout the fiber, or it may be partially on the surface and partially dispersed. In any case, the effective cross-sectional area A1 of the conducting medium is assumed to be constant along the length of the fiber.

The conductance measured between the ends of a length of fiber, L1 in length, is $$Gf = (\sigma A1)/L1 \tag{1}$$

where $\sigma$ is the conductivity of the medium. Thus, if L1 and $\sigma$ are known, the cross-sectional area A1 can be determined from the measurement of Gf. The value of A1 converts directly to the volume of conducting medium per unit length of fiber.

Figure 1:
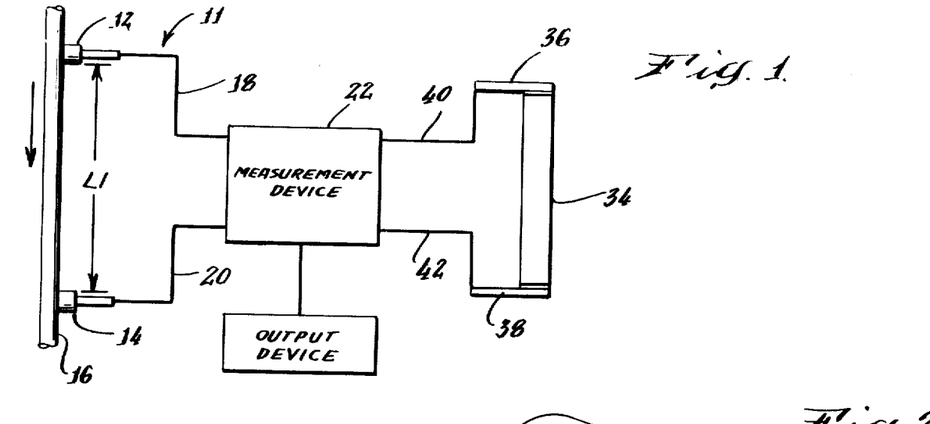
FIG. 1 is a schematic illustration of a filament contacted by electrical contact elements and a reference cell, each providing signals to a measurement circuit for providing an output indicative of the amount of finish on the filament in accordance with the invention.

In practice, several difficulties arise. One of these involves the making of electrical contact to the length of fiber to determine its conductance. Since the method is intended to be used on-line in a continuous process, it is clearly not possible to cut a length of fiber and apply end plates of some sort to it. Thus, contact configurations such as shown in FIG. 1 are necessary. As shown, a first electrical contact element 12 and a second electrical contact element 14 of a probe assembly 11 are positioned for sliding electrical contact with a moving filament 16. The contact elements are spaced along the path of the moving filament to define a conductive length L1 of filament. The contact elements 12 and 14 are connected by leads 18 and 20 to an electrical measurement circuit 22.

In order to guarantee a reliable indication of the conductance of a segment of fiber of length L1, it is necessary to make sure that the conductances of the contact-to-fiber interfaces are very large compared to the conductance of the fiber-medium of length L1, and that the longitudinal contacting dimensions of the contacts are small compared to L1. It is also necessary to insure that the contact arrangement is such that the contact to the moving fiber is maintained constantly.

Figures 2, 3:
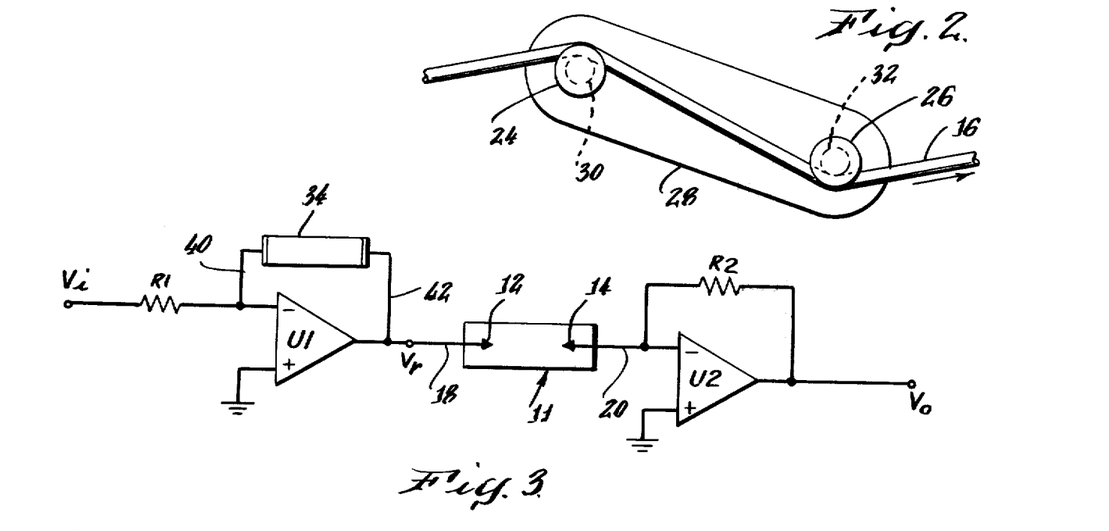
FIG. 2 is a side view of preferred contact elements for grasping a moving filament.
FIG. 3 is an electrical circuit diagram having the reference cell connected as the feedback resistance to a first operational amplifier and the length of filament connected as the input resistance of a second operational amplifier to provide an output voltage proportional to the ratio of the conductances.

The contact problem is most satisfactorily solved by using the contact configuration shown in FIG. 2. The contact elements are posts 24 and 26 extending outwardly from a pivotable plate 28. The posts have respective circumferential grooves 30 and 32 therein for receiving the filament 16. With the filament running between the two posts, the plate 28 can be pivoted about an axis normal to the page to tension the filament between the contact posts 24 and 26 as shown in FIG. 2. Thus, although the longitudinal contact of the filament is limited, a continuous and sufficient transverse contact is made by the contact elements.

Another problem involves the determination of the value of $\sigma$, the conductivity value of the finish medium that must be known to find A1. While apparently all water based finishes are good conductors (at least as compared to the fiber), values vary from finish to finish over at least two orders of magnitude. The determination of the value of $\sigma$ for the particular finish used would require extensive laboratory tests. Further, the conductivity of a particular finish is a function of temperature and of the age of the finish.

The problems involved in determining the value of $\sigma$ of the conducting medium are avoided with the present invention by providing a reference cell comprising a tube 34 filled with a sample of the same finish that is being applied to the fiber 16. The sample finish is contacted at either end of the reference cell 34 by contacts 36 and 38 which are connected through respective leads 40 and 42 to the measurement circuit 22.

The reference cell has a length L2 and an inner cross-sectional area A2. The conductance measured between its two ends is $$Gr = (A2\sigma)/L2 \tag{2}$$

where $\sigma$ has the same value for both the cell and the fiber measurement since the same finish is involved in both determinations. Thus, the value of $\sigma$ can be eliminated from the determination of A1 (the quantity of primary interest) by recognizing that $$Gf/Gr = (A1\sigma/L1)/A2\sigma/L2) \tag{3}$$

or $$A1 = (Gf\ A2L1)/(Gr\ L2) \tag{4}$$

It is only necessary to measure the ratio Gf/Gr and to scale it by a factor dependent on the above collection of geometric constants to determine A1.

The production finish measuring system embodiment includes one transducer per threadline. Thus, in order to be economically viable, it is necessary to design these portions of the system for low unit cost. Central equipment that is shared among many threadlines can be more complex.

A simplified schematic diagram for the production system is shown in FIG. 3. A stable voltage Vi is applied through an input resistor R1 to an operational amplifier U1. The sample cell 34 is connected as the feedback resistance across the operational amplifier U1. Thus, the stable voltage Vi is amplified by operational amplifier U1 to generate a reference voltage $$Vr = -Vi/R1\ Gr) \tag{5}$$

The reference voltage Vr is applied through the probe assembly 11 to the inverting input of an operational amplifier U2. A resistor R2 provides the feedback resistance across the operational amplifier U2. Thus, the system output voltage Vo is $$\begin{aligned}Vo &= \frac{Vi}{R1\ Gr}(R2\ Gf) \\ &= \frac{R2}{R1}Vi\frac{Gf}{Gr} \\ &= K\ Vi\frac{Gf}{Gr}\end{aligned} \tag{6}$$

Variables in the system should be scaled so that the various voltages are always below operational amplifier saturation levels for maximum anticipated finish density, yet are as large as possible, subject to this constraint, in order to minimize the effects of disturbing noise and the offset voltages of the operational amplifier. With the voltage Vi chosen to be in the order of 5 volts, resistor R1 should be selected approximately equal to 1/Gr. This selection results in the magnitude of the reference voltage Vr being in the desired range. Similarly, selection of resistor R2 approximately equal to 1/Gf for maximum anticipated finish densities leads to the maximum value of Vo being in the order of Vi. In the usual application, the conductance of the reference cell is a factor of 100 greater than the conductance of a fiber containing the maximum finish level. Thus the constant K should be selected equal to 100.

Figure 4A:
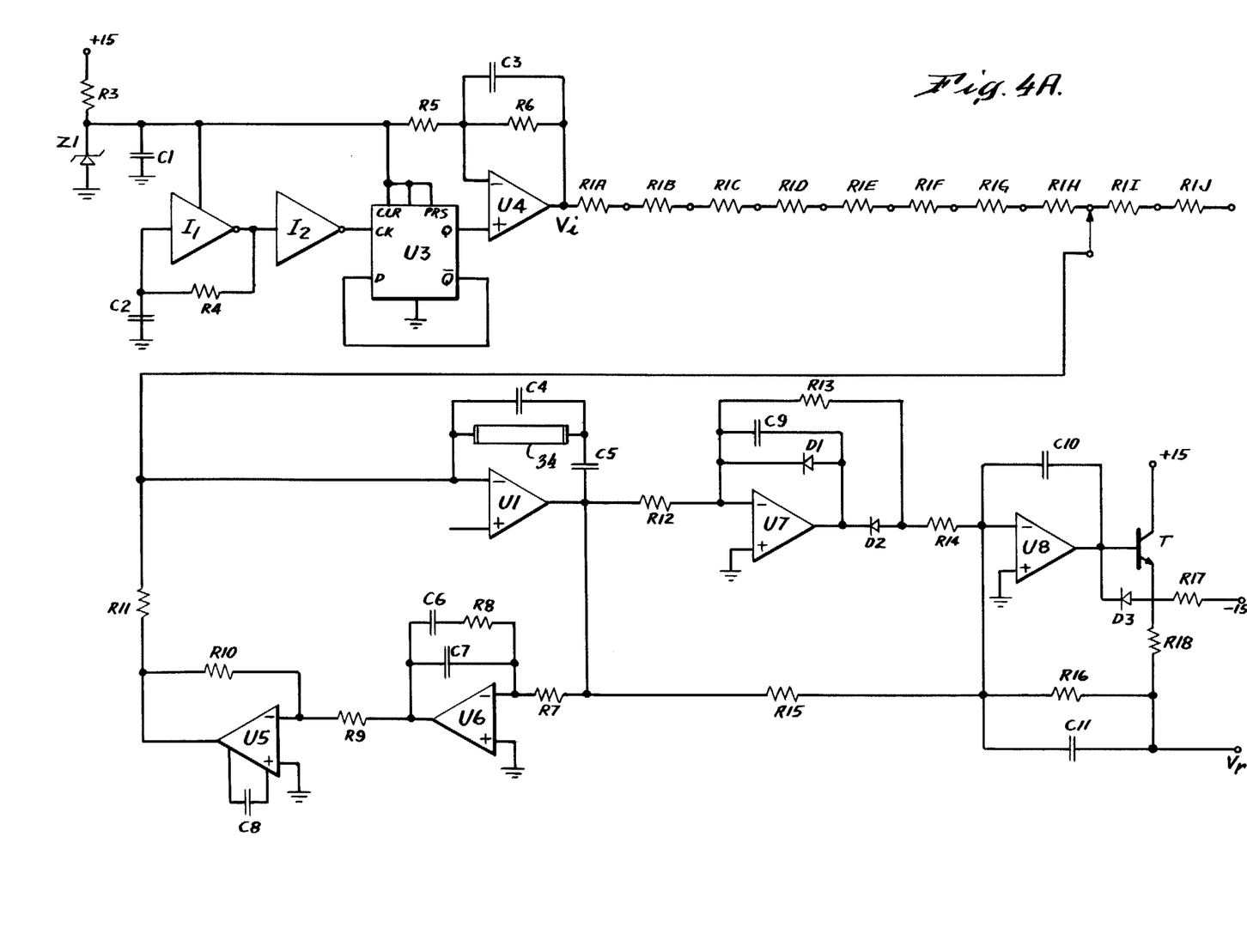
FIG. 4A is a detailed electrical circuit diagram of a preferred form of the left portion of the circuit of FIG. 3.
Figure 4B:
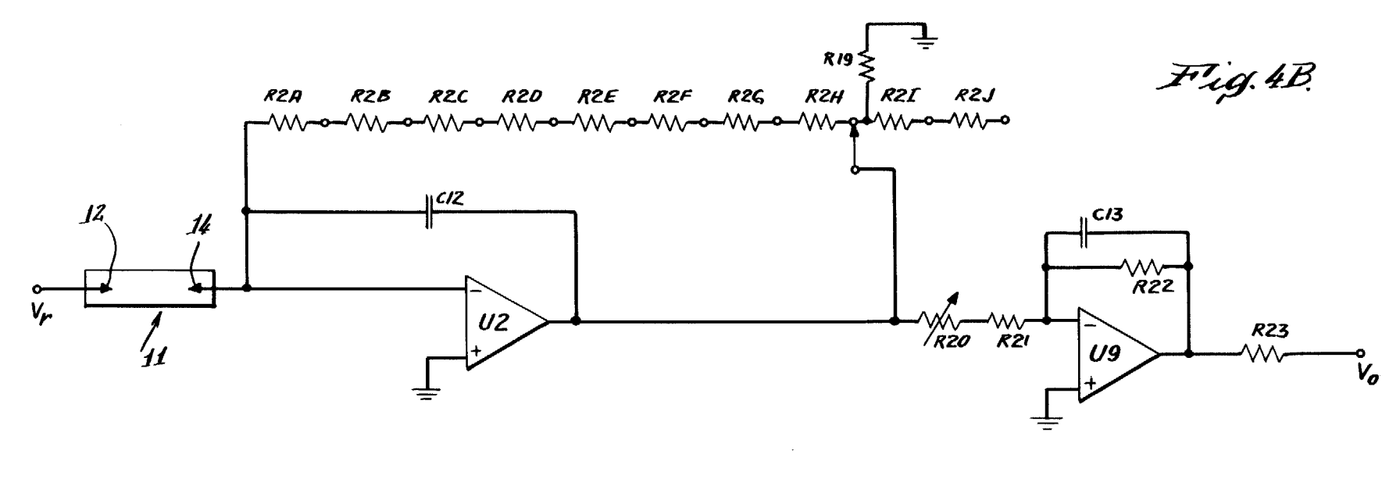
FIG. 4B is a detailed electrical circuit diagram of a preferred form of the right portion of the circuit of FIG. 3.

The actual circuit used for the production finish measuring system is shown in FIGS. 4A and 4B. The major difference between the actual system and the simplified one described above is forced because of electrochemical effects involving the finish (electrolyte) filled reference cell. With a dc voltage Vi, the electrolyte-filled reference cell acts as a battery that is discharged or charged. The magnitude of the effect is somewhat dependent on the electrodes used to contact the solution. However, if no dc current is passed through the cell, the battery effect is essentially eliminated. Thus, the actual circuit shown generates the reference voltage without passing dc current through the cell.

It is not necessary to eliminate dc current flow through the fiber, since the constantly changing electrolyte medium resulting from the fiber motion eliminates undesired electrochemical effects.

The reference generator corresponding to the left portion of FIG. 3 will be described with reference to FIG. 4A. CMOS logic circuits are powered from a stable voltage developed by a reference zener diode Z1. This voltage (nominally 6.4 volts) is applied to a Schmitt trigger oscillator, including inverter I1, and a D flip-flop U3 to generate a nominal 1.5 KHz square wave at the Q output of the flip-flop U3. An operational amplifier U4 converts this square wave to a symetrical plus or minus 6.4 volt square wave Vi. The square wave is applied to the operational amplifier U1 via a switchable resistor chain R1A through R1J. The switch position is selected for compatibility with the actual conductance of the reference cell. The cell itself is located in the feedback path of operational amplifier U1.

Even though the excitation for amplifier U1 is a square wave, dc current through the reference cell would result if the cell were connected directly across the amplifier for at least two reasons. First, offsets in amplifer U1 cause the square wave to include a dc component. Second, the input current of amplifier U1 would have to be supplied through the cell. To avoid dc current through the cell, a 5 μF, high quality capacitor C5 is included in series with the reference cell. With capacitor C5 there is no direct dc feedback path around operational amplifier U1, and, without additional feedback, its output would slowly drift into saturation. Operational amplifiers U5 and U6 provide the necessary direct coupled feedback path to force the average level at the output of operational amplifier U1 to zero. The feedback network C6, C7, R8 associated with operational amplifier U6 keeps this low frequency loop acceptably stable.

The signal at the output of amplifier U1 is nominally a zero-mean square wave, with a peak value proportional to 1/Gr, scaled as a function of the switch setting of resistor R1. Operational amplifiers U7 and U8, with associated components, form a precision rectifier and averager circuit. Buffering and protection are included since the output voltage of this circuit is the reference voltage distributed to all stations.

Since finish composition may change when new batches are added to the finish dispensing tank, some provision should be made to insure that the finish in the reference cell is representative of that being applied to the fiber at all times. One solution is to have the finish being applied actually flow through the reference cell on a continuous basis. If the conductivity of the finish changed sufficiently, it would be necessary to change the reference resistor R1 switch settings. For this purpose a detector could be included to signal when a switch setting change is required.

Each station transducer includes a probe assembly 11 monitoring the fiber conductivity as the input resistance of an inverting operational amplifier. The reference voltage Vr is applied to this circuit shown in FIG. 4B. The feedback resistor is made equal to 100 times the resistor selected for the reference generator by setting the station scale switch to the same setting as that used in the reference generator. This value of 100 is used because of the ratio between the reference cell conductance and the maximum fiber conductance as explained earlier. Thus it is necessary to change the settings of all of the station scale switches whenever the reference scale switch setting is changed. These changes can be made automatically by including some additional circuitry.

Because Gf can be as small as $10^{-8}$ mho for a low conductivity finish applied at a density of 20 mg/meter, it is necessary to use an FET input operational amplifier to minimize errors from amplifier input current.

Amplifier U9 with input trim resistor R20 allows adjustment of scale factor to the precisely desired value. It also provides electrical filtering to smooth the time varying signal that results from variable finish application levels. The time constant associated with the feedback network of this operational amplifier establishes the averaging time, and thus the effective fiber length over which finish level is averaged.

Figure 5:
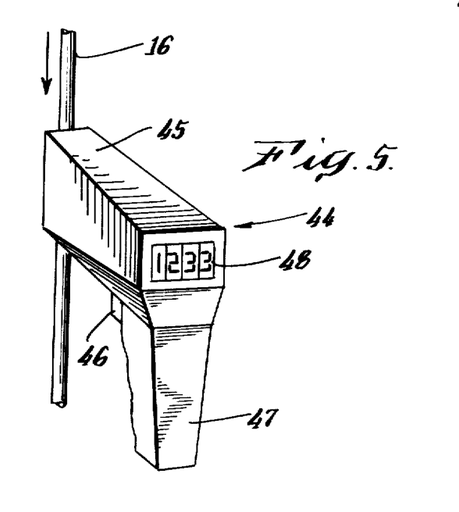
FIG. 5 is an isometric view of a hand-held measuring apparatus embodying the invention.

The above described production finish measuring system has a transducer probe 11 permanently positioned at various points in a system. In some production environments this is not feasible. Also, an exceptionally large number of transducer probes may be required in order to allow for trouble shooting within the system. The finish measuring instrument shown in FIG. 5 is in the form of a hand-held, portable unit 44 that can be used to measure any threadline in a production environment. The unit includes, at the end of its barrel 45, a probe having contact elements (not shown in FIG. 5) such as shown in FIG. 2. The unit is held by the handle 47 against a filament 16 and the pivotable plate 28 (FIG. 2) of the probe is pivoted by means of a trigger 46. When turned on, the unit automatically displays the quantity of finish medium per length of filament on the display panel 48. In this case, the display is for up to 19.99 milligrams per meter average finish level.

In the case of the portable unit, a major design objective is lower power consumption so that light-weight batteries can provide longer service. Since one instrument serves many threadlines in this implementation, economy is not as critical as with the multiprobe production system, and the circuit can be designed for improved accuracy as compared to the previous instrument.

Figure 6:
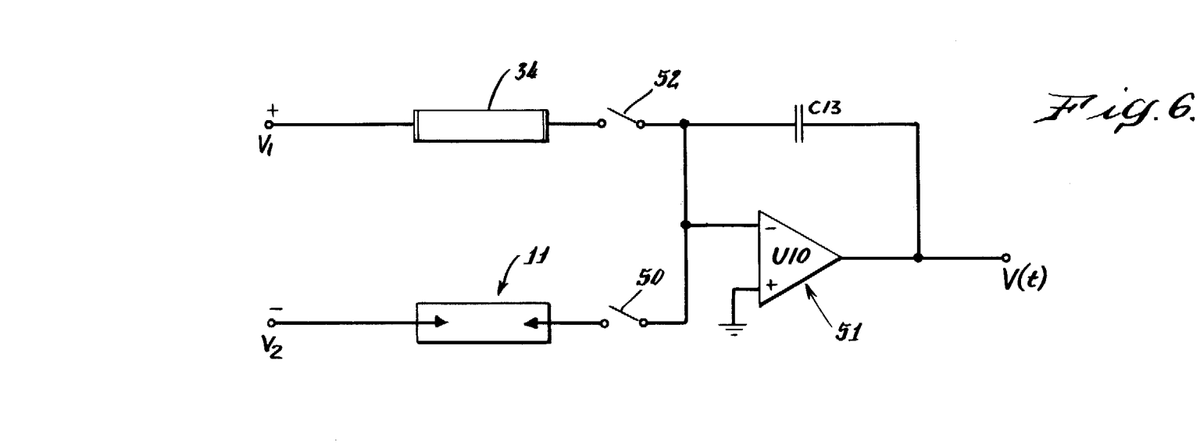
FIG. 6 is an electrical circuit diagram of an alternative embodiment of the invention in which voltages are applied through the length of filament and the reference cell to a dual slope circuit arrangement.

A simplified schematic diagram of the circuit used in the portable instrument 44 is shown in FIG. 6. In that figure, a positive voltage V1 is applied through the reference cell 34 and through a switch 52 to an integrator 51 including an operational amplifier U10 and a feedback capacitor C13. A negative voltage V2 is applied through the length of filament defined by probe 11 and through a switch 50 to the integrator 51.

The capacitor C13 associated with the operational amplifier U10 is assumed to be discharged at time t=0 with both switches 50 and 52 open. At t=0, the switch 50 is closed while switch 52 is left open. As a result, the slope of the signal V(t) at the amplifier output is positive (since V2 is negative), and the magnitude of this slope is $$dV(t)/dt = V2\ Gf/C \tag{7}$$

where C is the capacitance of C13.

This integrating state is maintained for a fixed period of time t1. At the end of this period, the magnitude of the voltage V(t) is $$V(t1) = V2\ Gf/C\ t1 \tag{8}$$

Figure 7:
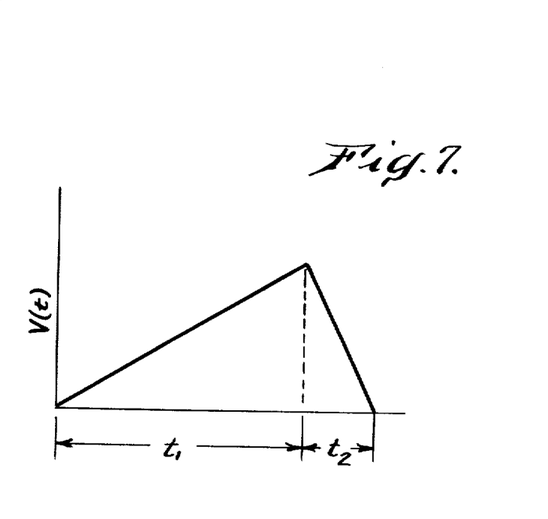
FIG. 7 is a graphical illustration of the wave form of the voltage V(t) from FIG. 6.

At time t=t1, switch 50 is opened and switch 52 is closed. Since voltage V1 is positive, the slope of the output voltage V(t) is negative. The time required for the signal V(t) to return to zero is t2 (FIG. 7), and $$t2 = V2/V1 \cdot Gf/Gr \cdot t1 \qquad (9)$$

Thus if the quantities t1, V1, and V2 are known, measurement of t2 determines the critical ratio Gf/Gr.

Figure 8A:
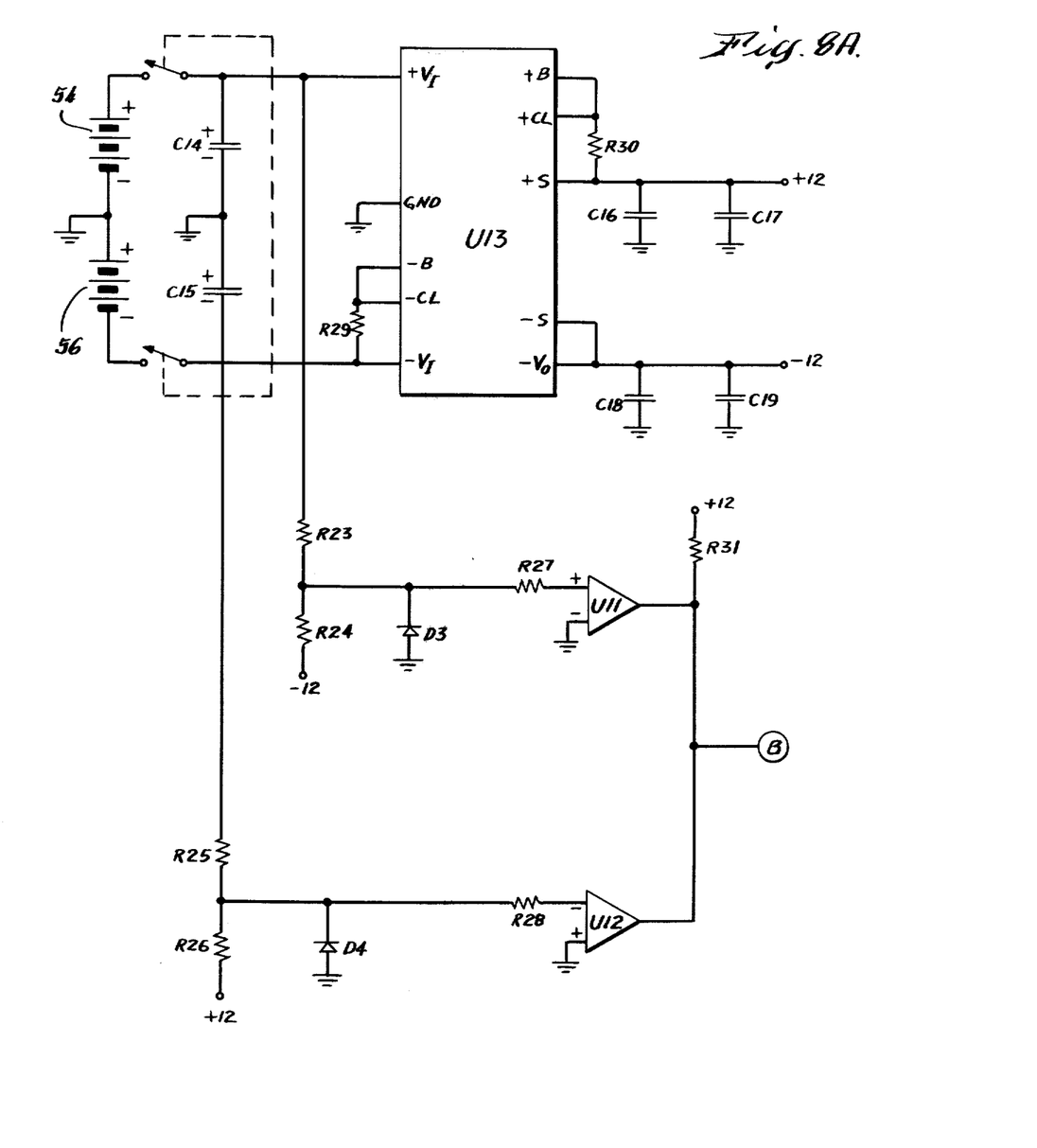
FIG. 8A is a detailed circuit diagram of a power supply used in a preferred form of the circuit of FIG. 6.
Figure 8B:
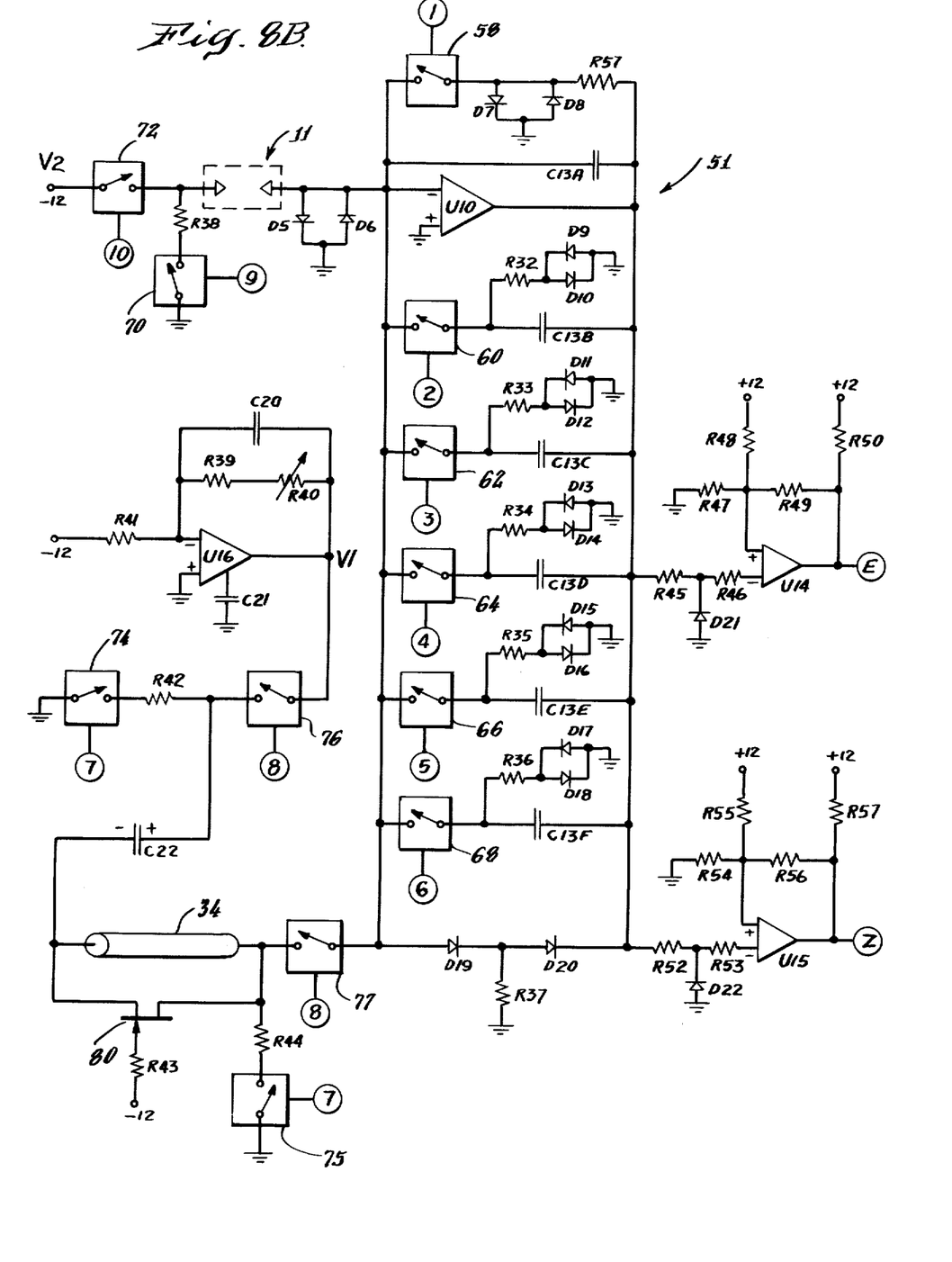
FIG. 8B is a detailed electrical circuit diagram of a preferred form of the analog circuit of FIG. 6.
Figure 8C:
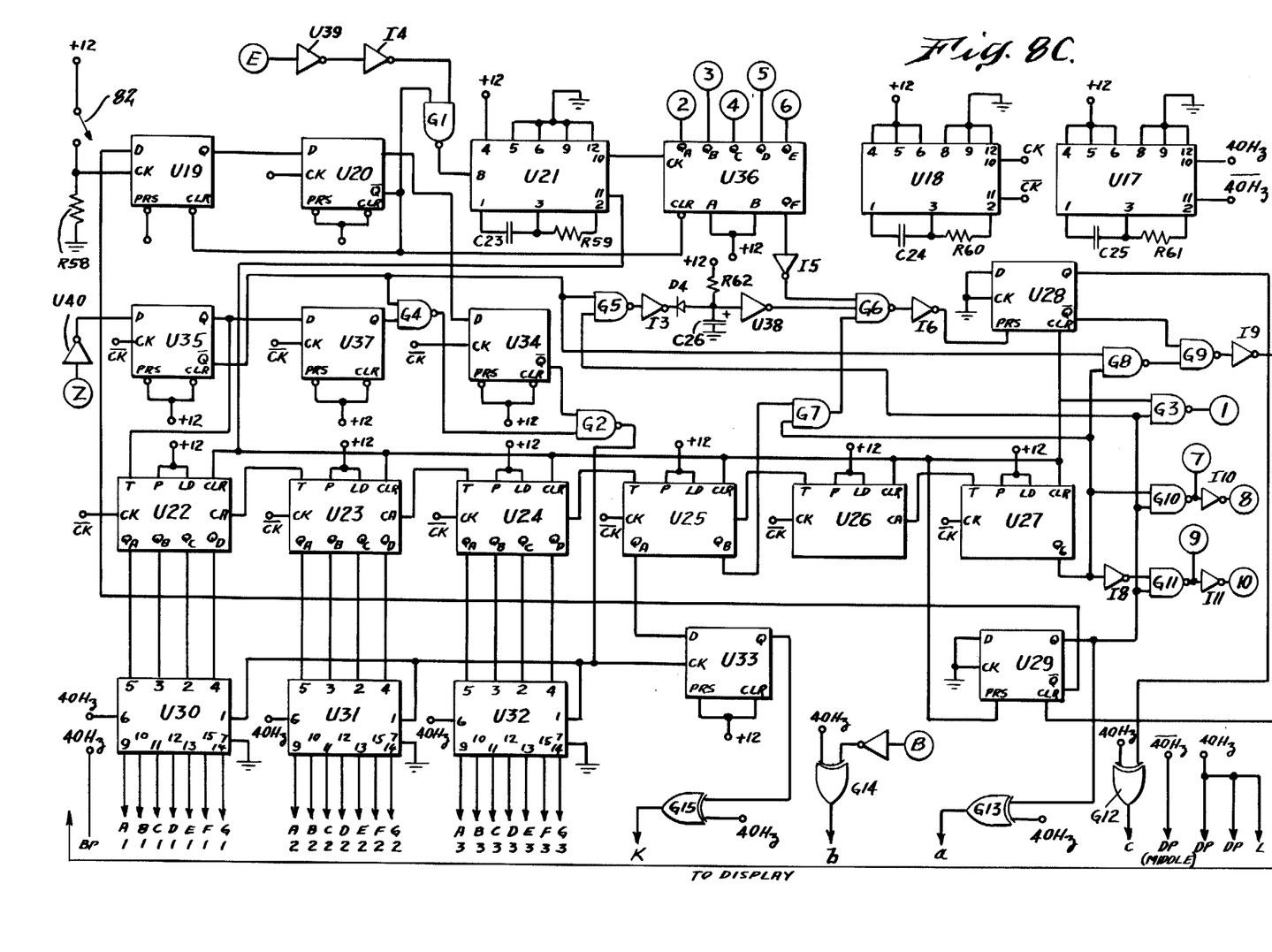
FIG. 8C is a detailed electrical circuit diagram of the digital control circuitry for controlling the analog circuit of FIG. 8B.

The complete schematic for this instrument is shown in FIGS. 8A, 8B and 8C, the power supply, analog portion and digital control portions of the system, respectively. In order to reduce power consumption, all of the digital portion is implemented using CMOS logic as are the switches in the analog portion. The display is a liquid-crystal type. Similarly, low power linear integrated circuits are used, and all associated components are scaled for low power.

With reference to FIG. 8A, the operating voltages for the circuits are obtained by regulating the nominal 22.5 volt output of batteries 54 and 56 in voltage regulation U13 to obtain ±12 volts. Comparators U11 and U12 are included to signal the logic for a low-battery display whenever the magnitude of either battery voltage drops below 18 volts. At this level, the circuit has an ample reserve voltage margin, so the warning is displayed prior to any performance degradation. Measurements indicate that the battery drain is less than 7 mA, so the batteries provide an operating lifetime of approximately 20 to 25 hours. An alternate power supply that obtains the operating voltages from a single, rechargeable battery is also possible.

The integrating operational amplifier U10 in FIG. 8B is shunted with a switch 58 driven by signal (1) from the digital control logic. Closing of this switch initializes all integrator capacitor voltages to zero prior to the start of a measurement cycle. At the start of the measurement cycle, the switch 58 driven by signal (1) is open, as are the switches 60, 62, 64, 66 and 68 driven by signal (2) through (6). Each of the switches 60 through 68 is associated with a capacitor C13B through C13F which may be switched into the circuit by signals (2) through (6) to change the capacitance of the integrator 51. Before a measurement cycle, switch 70 controlled by signal (9) is closed, and switch 72 controlled by signal (10) is open so that the probe 11 does not affect the integrator 51. Similarly, switches 74 and 75 controlled by signal (7) are closed and switches 76 and 77 controlled by signal (8) are open to disconnect the reference cell 34 from the integrator 51.

When a measuring cycle is initiated, the signals (9) and (10) reverse state and the switches 70 and 72, associated with the probe assembly, connect the minus 12 volt V2 to the input of operational amplifier U10 through the probe assembly. The switches associated with the reference cell keep the cell disconnected from the integrating amplifier. With switches 58 through 68 open, the integrator 51 includes amplifier U10 and capacitor C13A. The slope of the signal from the integrator is proportional to Gf during a time period t1.

Two voltage levels are monitored at the output of the integrator 51 by comparators U14 and U15. The lowest of these is approximately 0.25 volt, and the time at which the integrator output voltage passes through this level is indicated by a change in the state of the signal (Z). If a low-to-high transition of signal (Z) does not occur within two seconds after the start of the cycle, the conclusion is that either the conductivity of the finish is extremely low, or the finish density is extremely low, or the probes are not making reliable contact with the fiber. In any case, the circuitry indicates an out of range condition.

If the 0.25 volt crossing occurs within 2 seconds of the start of the cycle, the starting point for the period t1 is made coincident with the transition time. By allowing the integrator to reach 0.25 volt before starting the actual measurement cycle, the effects of any errors in initial conditions or from the start-up transient are minimized.

The period t1 is approximately 4 seconds. If the signal at the integrator output exceeds 7 volts before period t1 is completed, the signal (E) will undergo a high-to-low transition. This condition signifies that, because of the value of Gf relative to the capacitance of capacitor C13A, the integrator is in danger of saturation. Accordingly, the integrator is reset to zero by means of the switch 58 driven by signal (1), and the switch C13B, driven by signal (2), is closed so that the effective feedback capacitor size is increased to C13A plus C13B. The cycle then starts again. If a second overflow occurs, capacitor C13C is added in parallel with the other two. This effective gain ranging by means of capacitor selection is used so that, when the correct capacitor size is found, the measurement will be completed with a peak integrator output voltage at a level which prevents saturation and minimizes the effects of noise and operational amplifier offsets. This automatic gain ranging serves the same fundamental purpose as the resistor range switch setting operation described in connection with the production finish measuring system.

If the integrator output exceeds 7 volts in less than 4 seconds even with the maximum capacitor value, the circuitry detects and indicates an out of range condition. Note that the minimum and maximum permissible values of Gf can be scaled by changing all capacitors proportionately. Similarly, the dynamic range, or spread between allowable maximum and minimum values, can be increased by increasing the number of feedback capacitors and associated switches.

The various diodes and resistors in the integrator circuit serve to keep the voltages across open analog switches low, thus lowering their leakage current, and to keep the output of the integrator from going highly negative under startup conditions. Switch leakages must be controlled so that they do not interfere with extremely small signal currents that result from low values of Gf. The diodes associated with the comparators keep the inputs of these circuits from being forced negative, since that would cause a false indication.

Assuming that Gf is within the range of the integrator 51, the integrator output will be somewhere between approximately 2.3 volts and 7 volts a period of t1 (approximately 4 seconds) after the integrator 51 has been released following a reset by switch 58. This may occur with the switches 60 through 68 driven by signals (2) through (6) open, the switch 60 driven by signal (2) closed and all other switches open, and so on, or it may not occur until there have been 5 resets from excessive integrator output voltages resulting in the switches 60 through 68 driven by signals (2) through (6) all being closed.

After the 4 second integration interval has been completed with the integrator 51 output remaining within the desired range, the probe assembly 11 is disconnected from the integrator input by switches 70 and 72, and the reference cell is effectively connected between the output of an operational amplifier U16 and the integrator 51 input.

There is a capacitor C22 in series with the reference cell. This capacitor is to insure that no dc current flows through the reference cell in order to prevent the battery problem mentioned earlier. The capacitor is large relative to the integrator capacitors and thus provides only a small change in voltage thereacross. Thus, it can be assumed that the voltage applied to the reference cell during the discharge cycle is the voltage at the output of the amplifier U16.

The voltage for the second part of the integration cycle is obtained by scaling the voltage used for the first part of this cycle (−12 volts) with the amplifier U16. Since the measurement described is ratiometric, any variation in the −12 volt supply will not introduce a measurement error.

The second part of the integration cycle is completed when the signal (Z) goes high, indicating that the integrator output has dropped below 0.25 volt. At this time, the switches 76 and 77 driven by signal (8) are open, while switches 74 and 75 driven by signal (7) are closed. In this state, the voltage across the capacitor C22 returns to zero exponentially in such a way that the net dc current flow through the reference tube is zero over a complete cycle. When the total integration cycle is completed, the logic forces signal (1) high causing the switch 58 driven by the signal to close, thus resetting the integrator to a nominally zero volt output. This state is maintained until the next measurement cycle starts.

Hysteresis is used around the comparators U14 and U15 that provide the (E) and (Z) signals to eliminate the possiblity of multiple output transitions from these devices. A fairly wide hysteresis bond of 70 mv is used for the upper comparator, since hysteresis in this unit does not influence the measurement. The offset error associated with the measurement is related to the amount of hysteresis used with the lower comparator, and this value is held to approximately 5 mv to reduce this source of error.

The field-effect transistor 80 connected around the reference cell reduces battery drain. Under normal operating conditions, the gate of this transistor is biased below pinch off and it does not affect operation. However, when power is removed the gate bias is eliminated, and the transistor provides a low resistance shunt to keep the reference tube discharged.

The logic circuitry that controls the system is shown in FIG. 8C. Unit U17 provides a symmetrical 40 Hz square wave that is used to excite the liquid crystal display. Unit U18 is connected to provide a nominal 100 KHz square wave system clock.

A measurement is initiated by pushing the start button 82. Providing that a measurement is not in progress, the D input of flip-flop U19 will be high, and thus the flip-flop will be set to the Q=1 state. This state is transferred synchronously to flip-flop U20, whereupon flip-flop U19 is cleared. Flip-flop U20 provides one of two ANDed trigger inputs to a one-shot U21 which has a nominal 200 ms period. This one shot U21 resets the decade counter chain U22 through U27, clears flip-flop U28 (a flip-flop that would have been in the Q=1 state had the previous measurement been out of range), presets flip-flop U29 (this flip-flop indicates a measurement is in progress when it is in the Q=1 state), and forces signal (1) high so that the integrator reset switch 58 is closed for the duration of the one shot pulse.

The display buffers U30 through U33 are strobed during the clock interval immediately following the one shot trigger by flip-flop U34 and its following gate G2. Since the counter chain U22 through U27 is reset during this time, the display indicates 0000, preceded by a special symbol a (via busy flip-flop U29) to show the user that the measurement is in progress. Since the $\overline{Q}$ output of flip-flop U29 connects to the D input of the flip-flop U19, the flip-flop U19 cannot be retriggered to the Q=1 state while a measurement is in progress. The Q output of flip-flop U29, combined logically with the state of the counter chain from stage U27, at this time also makes signal (9) low and signal (10) high so that the probe assembly 11 is connected to the integrator input.

When the one shot U21 returns to its low state, signal (1) at the output of NAND G3 goes high and the integrating capacitor C13A is released. Assuming that Gf is sufficiently large, the signal (Z) (FIG. 8B) goes low a short time later. This transition of signal (Z) results in flip-flop U35 changing to the Q=1 state on the next clock pulse. The counter chain is thereby enabled and starts to count.

Assume that Gf is large enough so that the integrator output reaches +7 volts before the counter reaches a count of 400,000 (signified by QC=1 on counter U27) approximately 4 seconds later. In that case the signal (E) goes low with QC of U27 still 0. The one shot U21 is triggered again through gate G1, and the counter chain is reset to all 0's. This time the shift register U36 is advanced to the QA=1 state on the positive transition applied to its clock input. This state makes signal (2)=1, and increases the size of the feedback capacitor C13 as described earlier.

This process continues until the shift register has been incremented to the state necessary to prevent the integrator output voltage from exceeding 7 volts before the counter counts to 400,000 as signified by QC=1 on counter U27.

The 0 to 1 transition of the QC signal from counter stage U27 changes the states of signals (7), (8), (9) and (10) so that the probe is disconnected from the integrator and the reference cell is simultaneously connected to this operational amplifier.

At this time counters U22 through U25 have cycled to all 0's, and so begin to count up again. Because it is known that the value of Gr will be much larger than the value of Gf, even with the full-scale finish density of 20 mg/meter, the duration of the second portion of the integration cycle is much shorter than that of the first. This difference is reflected by the fact that only the counter states that can represent a maximum count of 1999 are connected to the display drivers.

The scale factor of the output is determined by a variable resistor R40, adjustment of which provides system calibration (FIG. 8B).

The second half of the integration cycle ends when the signal (Z) changes from low to high, indicating that the integrator output has dropped below 0.25 volt. At this instant the number in the counter chain corresponds to the finish level in mg/meter if the system is properly calibrated. Flip-flops U35 and U37 and associated gates G4 and G2 generate a pulse with a single clock period width at this time, and this pulse strobes the number in the counter chain into the display drivers U30 through U33.

Three separate conditions can set the U28 flip-flop to the Q=1 state, and this state indicates an out-of-range situation. If signal (Z) does not go low within approximately 2 seconds after the start of a measurement cycle, the conclusion is that the value of Gf is too small or that probe is not making contact with the fiber. This condition is determined by a network consisting of a capacitor C26 and a resistor R62. When flip-flop U29 is preset by one-shot U21 the output of NAND gate G5 goes low. The output of inverter I3 then goes high and capacitor C26 begins to charge through resistor R62. If the voltage on capacitor C26 reaches the threshold of the associated device U38 before (Z) goes low, a preset signal is applied to flip-flop U28 through NAND gate G6. On the other hand, a low (Z) input causes capacitor C26 to discharge through diode D4.

A second out-of-range condition results if the quantity Gf is too large. In this case, the automatic gain ranging will eventually result in QF=1 for shift register U36, and that level sets the out-of-range flip-flop U28 to Q=1. The final possibility is that Gf is not large enough to cause difficulty with the integrator dynamic range, but does correspond to a finish level in excess of 20 mg/meter. This condition causes the number in the counter to exceed 1999 during the second part of the integration cycle. The AND (G7) combination of the QB output of counter U25 with QC of counter U27 indicates this situation, and is the third possible way to set flip-flop U28. If the out-of-range condition is detected, a special symbol c on the display is turned on, and the flip-flop U29 is cleared to end the measurement cycle.

The second possibility for ending the measurement cycle involves (Z) going high with the second half of the integration cycle in progress; that is with the output of integrator 51 dropping below 0.25 volts. This is, of course, the normal end of the cycle that results when no out-of-range condition is detected. Another gate G8 detects this combination. Whenever the end of a measurement occurs, both the probe assembly 11 and the reference cell 34 are disconnected from the integrator with clearing of the flip-flop U29, and low impedance paths R38 and R42 (FIG. 8B) are connected around the probe 11 and cell 34. Signal (1) is also forced high through gate G3 so that the integrator 51 is reset.

The special symbol b included in the display is turned on if a low battery condition is signified by (B)=0 (FIG. 8B).

It is apparent from the above description of the handheld, portable filament measuring instrument that the instrument can readily be positioned adjacent a filament. Thereafter, the instrument automatically sets the integrating circuit to an optimum setting for giving maximum sensitivity and accuracy. Due to the use of a reference cell, complicated calibration techniques are not required for use with various filament finishes. The one using the instrument need only provide a sample of the finish medium, position the pistol-like instrument adjacent a filament, push the trigger button to grasp the filament in the probe assembly, and turn on the measuring circuit. Within seconds, the quantity of finish per unit length of filament is automatically determined and displayed.

In FIG. 4A, the following circuit values have been used in a successful finish measuring apparatus:

| | |
|---|---|
| R1A, R1B | 2.49K |
| R1C | 4.99K |
| R1D | 10K |
| R1E | 20K |
| R1F | 40.2K |
| R1G | 80.6K |
| R1H | 162K |
| R1I | 324K |
| R1J | 634K |
| R3 | 1.5K |
| R4 | 100K |

-continued

| | |
|---|---|
| R5 | 100K |
| R6 | 100K |
| R7 | 1M |
| R8 | 2.7M |
| R9, R10 | 10K |
| R11 | 270K |
| R12 | 10K |
| R13 | 10K |
| R14 | 100K |
| R15, R16 | 200K |
| R17 | 1K |
| R18 | 100 |
| C1 | .1μF |
| C2 | 220pF |
| C3, C4 | 10pF |
| C5 | 5μF |
| C6 | .39μF |
| C7 | .39μF |
| C8 | 100pf |
| C9 | 29pF |
| C11 | 1μF |

In FIG. 4B the following circuit values have been used:

| | |
|---|---|
| R2A, R2B | 249K |
| R27 | 499K |
| R2D | 1M |
| R2E | 2M |
| R2F | 4.02M |
| R2G | 8.06M |
| R2H | 16.2M |
| R2I | 10K |
| R2J | 20K |
| R19 | 10K |
| R20 | 200K Trim Pot |
| R21 | 536K |
| R22 | 1M |
| R23 | 100 |
| C12 | 10pF |
| C13 | 1μF |

In FIG. 8A the following circuit values have been used:

| | |
|---|---|
| R23 | 150K |
| R24 | 100K |
| R25 | 150K |
| R26 | 100K |
| R27, R28 | 10K |
| R29, R30 | 22 |
| R31 | 100K |
| C14, C15 | 6.A μF. |
| C16 | 15μF |
| C17 | .1μF |
| C18 | 15μF |
| C19 | .1μF |

In FIG. 8B the following circuit values have been used:

| | |
|---|---|
| R32-R38 | 1K |
| R39 | 40.2K |
| R40 | 50K Trim Pot |
| R41 | 150K |
| R42 | 4.7K |
| R43 | 100K |
| R44 | 4.7K |
| R45, R46 | 10K |
| R47 | 68K |
| R48 | 47K |
| R49 | 4.7M |
| R50 | 100K |
| R51 | 4.7K |
| R52, R53 | 10K |

| -continued | |
|---|---|
| R54 | 4.7K |
| R55 | 220K |
| R56 | 10M |
| R57 | 100K |
| C13A | 1500pF |
| C13B | 3300pF |
| C13C | .01µF |
| C13D | .033µF |
| C13E | .1µF |
| C13F | .33µF |
| C20 | 22pF |
| C21 | 1000pF |
| C22 | 15µF |

The following circuit values have been used in the circuit of FIG. 8C:

| | |
|---|---|
| R58 | 47K |
| R59 | 220K |
| R60 | 47K |
| R61 | 220K |
| R62 | 330K |
| C23 | .18µF |
| C24 | 24pF |
| C25 | .022µF |
| C26 | 6.8µF |

While the invention has been particularly shown and described with reference to a preferred embodiment thereof, it will be understood by those skilled in the art that various changes in form and details may be made therein without departing from the spirit and scope of the invention as defined by the appended claims.

What is claimed is:

1. A measuring apparatus for measuring the amount of an electrically conductive medium applied to a moving filament comprising:
    a first electrical, filament contact element positionable adjacent said filament for sliding electrical contact therewith;
    a second electrical, filament contact element spaced from said first filament contact element along the path of said moving filament and positionable for sliding electrical contact with said filament, said first and second filament contact elements defining a conductive length of filament;
    a reference cell of predetermined dimensions containing a sample of said electrically conductive medium, and having spaced electrical contact elements in electrical contact with said contained sample; and
    electrical circuit means connected to said filament contact elements and to said reference cell contact elements for determining the amount of said electrically conductive medium applied to said filament as a function of the ratio of the conductance of said length of filament to the conductance of said sample.

2. A measuring apparatus as claimed in claim 1, said apparatus being a portable, hand-held measurement apparatus and further comprising:
    means for selectively grasping said filament and holding said filament in sliding electrical contact with each of said filament contacts.

3. A measuring apparatus as claimed in claim 1 wherein said electrical circuit means comprises:
    a first operational amplifier;
    an input resistance connected to said first operational amplifier;
    one of said length of filament and said sample being connected through respective ones of said contact elements across said first operational amplifier as a feedback resistance;
    a second operational amplifier in series with said first operational amplifier;
    a feedback resistance connected across said second operational amplifier; and
    the other of said length of filament and said sample being connected through respective ones of said contact elements as an input resistance to said second operational amplifier.

4. A measuring apparatus as claimed in claim 3 wherein:
    said sample is connected through said reference cell contact elements across said first operational amplifier as said feedback resistance; and
    said length of filament is connected through said filament contact elements as said input resistance to said second operational amplifier.

5. A measuring apparatus as claimed in claim 3 wherein an ac signal is applied to said electrical circuit means and said sample is ac coupled to said circuit means to prevent the electrochemical effects resulting from dc current flow through said sample.

6. A measuring apparatus as claimed in claim 3 wherein said input resistance connected to said first operational amplifier and said feedback resistance connected across said second operational amplifier are each variable scaling resistors for optimizing the sensitivity range of the circuit means relative to the particular conductive medium applied to said filament.

7. A measuring apparatus as claimed in claim 6 wherein said variable input resistance and said variable feedback resistance have interrelated variability in order that the scaling of the output signal remains constant with changes in the sensitivity range of the circuit means.

8. A measuring apparatus as claimed in claim 1 wherein said electrical circuit means comprises:
    means for integrating a voltage applied through said length of filament over a first period of time to provide an integrated voltage;
    means for integrating a voltage applied through said sample over a second period of time to provide said integrated voltage;
    means for determining the ratios of said first and second periods of time.

9. A measuring apparatus as claimed in claim 1 wherein said electrical circuit means comprises:
    an integrator for providing an integrated voltage;
    a first switch for connecting a voltage to said integrator across said length of filament;
    a second switch for connecting a voltage to said integrator across said sample;
    a control circuit for alternately closing said first and second switches and for comparing the respective times for said integrated voltage to have equal changes in value with respective ones of said switches closed.

10. A measuring apparatus as claimed in claim 9 wherein said integrator is an integrating operational amplifier.

11. A measuring apparatus as claimed in claim 9 including means for detecting when said electrical circuit is operating in other than an optimum sensitivity range and for adjusting the parameters of said integrator so that said integrator operates in an optimum sensitivity range.

12. A measuring apparatus as claimed in claim 9 wherein said electrical circuit means further comprises threshold circuit means for setting a measurement threshold for said integrated voltage.

13. A measuring apparatus as claimed in claim 9 wherein said sample is ac coupled to said electrical circuit means to prevent the electrochemical effects resulting from dc current flow through said sample.

14. A measuring apparatus as claimed in claim 1 wherein said sample is ac coupled to said electrical circuit means to prevent the electrochemical effects resulting from dc current flow through said sample.

15. A portable, hand-held measuring apparatus for measuring the amount of electrically conductive medium applied to a moving filament comprising:
- a first electrical, filament contact element positionable adjacent said filament for sliding electrical contact therewith;
- a second electrical, filament contact element spaced from said first contact element and positionable for sliding electrical contact with said filament so that said first and second filament contact elements define a conductive length of filament;
- means for selectively grasping said filament and holding said filament in sliding contact with each of said filament contacts; and
- electrical circuit means connected to said filament contacts for determining the amount of said electrically conductive medium applied to said filament as a function of the composite conductance of said filament and said medium;
- said electrical circuit means comprising first means to apply an electrical signal to said filament contact elements to produce a flow of current therethrough responsive to said composite conductance;
- said electrical circuit means comprising second means coupled to said contact elements for measuring the magnitude of said current flowing through said contact elements and to produce a signal calibrated to represent the quantity of finish on said filament between said contact elements.

16. A portable, hand-held measuring apparatus as claimed in claim 15 wherein said means for selectively grasping said filament comprises:
- a pivotable plate to which said first and second filament contact elements are mounted, said filament being pushed in opposite directions by said filament elements with pivoting of said plate.

17. A method of measuring the amount of an electrically conductive medium applied to a moving filament comprising the steps of:
- providing spaced, electrical, filament contact elements in large-area high-conductance sliding electrical contact with said filament;
- providing a reference cell containing a sample of said electrically conductive medium and having spaced electrical contact elements in electrical contact with said contained sample; and
- producing by an electrical circuit a measurement signal which is proportional to the ratio of the conductance of said length of filament to the conductance of said sample.

18. The method of measuring the amount of an electrically conductive medium applied to a moving filament as claimed in claim 17 wherein said filament contact elements are positioned on a hand-held instrument and said hand-held instrument includes means for selectively grasping said filament and holding said filament in sliding electrical contact with each of said filament contacts.

19. The method of measuring the amount of an electrically conductive medium applied to a moving filament as claimed in claim 17 wherein said sample is connected across a first operational amplifier as a feedback resistance, and said length of filament is connected as the input resistance to a second operational amplifier in series with the first.

20. A method for measuring the amount of an electrically conductive medium applied to a moving filament as claimed in claim 17 wherein voltages are alternately applied through said length of filament and through said sample to a dual slope integrating circuit.

21. A method of measuring the amount of an electrically-conductive medium applied to a moving filament comprising the steps of:
- pressing large-area contact elements against said moving filaments at longitudinally-spaced regions thereof;
- developing a flow of current through said contact elements and the portion of said filament therebetween;
- developing a flow of current through a separate sample of electrically-conductive medium matching said medium on said moving filament;
- producing by electrical circuit means responsive to said current flows a measurement signal proportional to the relative conductances of said sample medium and said medium on said moving filament.

22. The method of claim 21, including the step of developing a flow of alternating current through said sample medium, to avoid the harmful effects of direct current flow through the sample medium.

23. A portable, hand-held measuring apparatus for measuring the amount of electrically conductive medium applied to a moving filament comprising:
- a unitary housing;
- a manually-graspable handle secured to said housing to permit an operator to hold the housing in a position adjacent a moving filament;
- said housing carrying a first electrical filament contact element positionable for slidng electrical contact with said moving filament;
- said housing carrying a second electrical filament contact element spaced from said first contact element and positionable for sliding electrical contact with said filament so that said first and second filament contact elements define a conductive length of filament therebetween;
- said first and second contact elements presenting smooth large-area surfaces to provide effective continuous sliding contact with said filament and having contact conductances substantially greater than the conductance of said medium between said two contact elements;
- electrical circuit means connected to said filament contact elements for producing an electrical measurement signal representing the amount of said electrically conductive medium applied to said filament as a function of the conductance of said filament; and
- a read-out instrument mounted in one exterior surface of said housing and located to be viewed by the operator while said housing is manually held by the operator in position adjacent the moving filament with said contact elements in sliding contact therewith, said read-out instrument presenting to the operator a reading corresponding to said electrical measurement signal.

24. In a process for forming a fiber to be incorporated in a product such as a textile fabric, wherein during the processing sequences a liquid finish is applied to the surfaces of the fiber to aid in the processing thereof, and wherein it is important in achieving good product quality to measure and control the amount of finish that has been applied in order to provide for application of finish to within limits appropriate to said fiber processing, the improvement comprising;

a method of measuring the quantity of finish that has been applied to the fiber, wherein the measurement is made on-line, while the fiber is moving during said processing, and with the finish in moist condition, to provide a continuous reading of the quantity of finish that has been applied progressively along the length of the moving fiber; said method comprising the steps of:

pressing first and second contact elements against the moving fiber at longitudinally separated points along the fiber;

developing a flow of current serially through said contacts and the length of said finish-treated fiber disposed therebetween, at least part of said current flowing through the moist finish;

sensing the magnitude of said current flow; and developing an electrical measurement signal in accordance with said sensed current flow and corresponding to the composite conductance of said length of finish-treated fiber and the moist finish thereon, as determined by the electrical characteristics of said fiber and the amount of moist finish between said contact elements, said measurement signal being calibrated to represent the quantity of said finish on the portion of the moving fiber between said elements.

25. The method of claim 24, including the steps of:
developing a reference current by applying a predetermined voltage to a reference element having a preselected conductance;
developing a reference signal proportional to said pre-determined voltage;
applying said reference signal to said contact elements to produce said flow of current through said fiber; and
developing said measurement signal in accordance with the ratio of the reference current and flow of current through the contact elements.

26. The method of claim 25, wherein the ratio of said two currents is determined by an integrating-circuit wherein:
said flow of current is applied to said circuit to cause it to integrate in one direction from an original starting level for a pre-set period of time; and
said reference current is applied to said integrating circuit to cause it to integrate in the opposite direction until it reaches said original starting level, whereby the time of integration with said reference current is a measure of the ratio of the two currents.

27. The method of claim 25, wherein said reference current is developed by applying a voltage to a reference cell containing a quantity of the finish applied to said fiber.

28. The method of claim 27, wherein said voltage applied to said reference cell is an a-c voltage.

29. A method of measuring the amount of finish applied to a moving filament comprising the steps of:
pressing large-area contact elements against said moving filament at longitudinally-spaced regions thereof;
developing through said contact elements and the portion of said filament therebetween a first flow of current having a magnitude proportional to the conductance of said finish on said filament portion;
developing through an electrically-conductive element a second flow of current having a magnitude which is substantially constant and proportional to the conductance of said element, said element conductance bearing a pre-determined relationship to the conductance of said finish; and
producing by electrical circuit means responsive to the ratio of said first and second current flows a measurement signal proportional to the relative conductances of said finish on said portion of moving filament and said element respectively, whereby to provide a continuous measure of the amount of said finish carried by said moving filament.

30. The method of claim 29, including the steps of:
developing a sensor voltage responsive to said second flow of current;
applying to said contact elements a voltage derived from said sensor voltage to produce said first flow of current; and
producing said measurement signal in the form of a measurement voltage proportional to said first flow of current.

31. The method of claim 29, wherein said first and second currents are developed by respective signals derived from a common source of voltage, whereby the ratio of currents represents the desired measurement unaffected by changes in the voltage source.

32. Measuring apparatus for determining the amount of finish applied to a moving filament comprising:
a first electrical contact element positionable adjacent said filament for sliding electrical contact therewith;
a second electrical contact element spaced from said first contact element along the path of said moving filament and positionable for sliding electrical contact with said filament, said first and second filament contact elements defining therebetween a length of filament carrying said finish;
means providing a voltage signal having a preselected magnitude;
reference means comprising a resistive electrical element having a conductance bearing a pre-determined relationship to the conductance of said finish and connected to said pre-selected voltage to produce a reference current proportional to said element conductance;
means developing a reference signal proportional to said pre-selected voltage magnitude;
electrical circuit means connecting said reference signal to said filament contact elements to produce a current therethrough proportional to the quantity of finish between said elements; and
means for developing a measurement signal responsive to the ratio of said finish current and said reference current to provide a measure of the amount of finish on the filament.

* * * * *